US00PP33904P2

(12) United States Plant Patent
Li

(10) Patent No.: US PP33,904 P2
(45) Date of Patent: Jan. 25, 2022

(54) ***VERBENA* PLANT NAMED 'KLEVP20037'**

(50) Latin Name: ***Verbena* x *hybrida***
Varietal Denomination: KLEVP20037

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/332,583

(22) Filed: May 27, 2021

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86
See application file for complete search history.

(56) References Cited

PUBLICATIONS

CPVO documentation for a *Verbena* plant named, 'KLEVP20037', serial No. 20211179, filed Apr. 28, 2021.*
UPOV hit on PLUTO for a *Verbena* plant named, 'KLEVP20037', QZ PBR 20211179, filed Apr. 29, 2021.*

* cited by examiner

*Primary Examiner* — Anne Marie Grunberg
(74) *Attorney, Agent, or Firm* — Weatherly IP Solutions, LLC; Barbara Campbell

(57) ABSTRACT

A new *Verbena* plant particularly distinguished by burgundy flowers, and an upright, compact, and rounded habit, is disclosed.

1 Drawing Sheet

Genus and species: *Verbena* x *hybrida*.
Variety denomination: 'KLEVP20037'.

BACKGROUND OF THE NEW PLANT

The present invention comprises a new and distinct variety of *Verbena*, botanically known as *Verbena* x *hybrida*, and hereinafter referred to by the variety name 'KLEVP20037'. 'KLEVP20037' originated from a cross-pollination conducted in November 2014 in Cobbitty, New South Wales, Australia between the proprietary female *Verbena* variety '14.0109' (unpatented), and the proprietary male *Verbena* variety '06.0057' (unpatented).

The seeds from the cross were sown and plants were grown for evaluation, where an individual plant designated 'KLEVP20037' was selected from the group of plants in Cobbitty, New South Wales, Australia in October 2015.

In October 2015, 'KLEVP20037' was first vegetatively propagated by vegetative cuttings in Cobbitty, New South Wales, Australia. 'KLEVP20037' was found to reproduce true to type in successive generations of asexual propagation via vegetative stem cuttings.

SUMMARY

The following are the most outstanding and distinguishing characteristics of this new variety when grown under normal horticultural practices in Latina, Italy.

1. Burgundy flowers; and
2. An upright, compact, and rounded habit.

DESCRIPTION OF THE PHOTOGRAPH

This new *Verbena* plant is illustrated by the accompanying photograph which shows the plant's overall plant habit including form, foliage, and flowers. The photograph is of a plant approximately 12-weeks-old grown indoors in Stuttgart, Germany in April 2020. The colors shown are as true as can be reasonably obtained by conventional photographic procedures.

DESCRIPTION OF THE NEW VARIETY

The following detailed descriptions set forth the distinctive characteristics of 'KLEVP20037'. The data which define these characteristics were collected from asexual reproductions carried out in Latina, Italy. Data was collected on three-month-old plants grown in a greenhouse in 2019. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—*Verbena*.
- *Designation*.—'KLEVP20037'.

Parentage:
- *Female parent*.—'14.0109' (unpatented).
- *Male parent*.—'06.0057' (unpatented).

Plant:
- *Growth and branching habit*.—Upright with a compact and round shape.
- *Height* (*from top of soil*).—22.0 cm.
- *Width* (*horizontal plant diameter*).—30.0 cm.
- *Time to produce a finished flowering plant*.—Approximately 8 weeks.
- *Time to initiate and develop roots*.—2 weeks.

*Root description*.—RHS 155B (White), fine fibrous roots.

Stems:

*Number of branches per plant*.—More than 26.
*Growth habit*.—Upright.
*Length*.—20.0 cm.
*Diameter*.—0.25 cm.
*Internode length*.—1.8 cm.
*Color*.—RHS 139D (Green).
*Anthocyanin*.—Absent.
*Texture*.—Pubescent.
*Appearance in cross-section*.—Round.

Leaves:

*Arrangement*.—Opposite.
*Immature and mature leaf color*.—Upper surface: RHS 141A (Green). Lower surface: RHS 141C (Green).
*Length*.—4.2 cm.
*Width*.—2.4 cm.
*Shape*.—Lanceolate.
*Apex*.—Acute.
*Base*.—Obtuse.
*Margin*.—Crenate.
*Texture*.—Upper surface: Leathery. Lower surface: Rugose.
*Venation type*.—Pinnate.
*Venation color* (*both upper and lower surfaces*).—RHS 141D (Green).
*Petioles*.—Length: 0.2 cm. Diameter: 0.1 cm. Color: RHS 141D (Green). Texture: Leathery.

Flower buds:

*Shape*.—Tall, cylindrical.
*Length*.—1.9 cm.
*Diameter*.—0.3 cm.
*Color* (*at tight bud*).—RHS N74C (Red-Purple).

Inflorescence:

*Blooming habit* (*flowering season*).—Continuously.
*Lastingness of individual blooms on the plant*.—About 1 week.
*Fragrance*.—Absent.
*Inflorescence type*.—Umbel.
*Length of inflorescence*.—3.4 cm.
*Diameter of inflorescence*.—5.2 cm.
*Number of florets per inflorescence*.—22.
*Peduncle*.—Color: RHS 141A (Green). Length: 2.3 cm. Diameter: 0.2 cm.

Florets:

*Length*.—2.1 cm.
*Diameter*.—2.1 cm.
*Texture*.—Smooth.
*Form*.—Single.
*Corolla tube length*.—1.7 cm.
*Corolla tube color*.—RHS 157B (Green-White).
*Petals*.—Length of lobe: 1.1 cm. Diameter of lobe: 0.7 cm. Lobe shape: Obtuse. Apex: Emarginate. Base: Fused. Margin: Entire. Texture (both upper and lower surfaces): Glossy, satiny. Color: Immature: Upper surface: RHS 71B (Red-Purple). Lower surface: RHS 70A (Red-Purple). Mature: Upper surface: RHS 71C (Red-Purple). Lower surface: RHS 70B (Red-Purple).
*Pedicels*.—Not visible.

Sepals:

*Shape*.—Lanceolate.
*Apex*.—Acute.
*Base*.—Fused.
*Margin*.—Entire.
*Length*.—1.1 cm.
*Diameter*.—0.2 cm.
*Color*.—RHS 141C (Green).
*Texture* (*both upper and lower surfaces*).—Hairy, dull.

Reproductive organs:

*Stamens*.—Present. Quantity: 4. Appearance: Didynamous. Color: RHS 139D (Green). Filament length: 0.2 cm. Filament diameter: 0.1 cm. Anther: Shape: Elliptic. Color: RHS 141D (Green). Length: 0.2 cm. Diameter: 0.1 cm. Pollen amount: Sparse. Pollen color: RHS 1B (Green-Yellow).
*Pistils*.—Quantity: 1. Length: 1.6 cm. Diameter: 0.1 cm. Stigma: Color: RHS 141D (Green). Appearance: Ovate. Length: 0.1 cm. Diameter: 0.1 cm. Style: Color: RHS 141D (Green). Length: 1.4 cm. Diameter: 0.1 cm. Appearance: Long.

Fruit and seed set: None observed.

Disease and pest/insect resistance: Good tolerance to powdery mildew (*Podosphaera xanthii*).

COMPARISON WITH PARENTAL LINES AND KNOWN VARIETY

'KLEVP20037' is distinguished from its parents as described in Table 1.

TABLE 1

Comparison with Parental Lines

| Characteristic | 'KLEVP20037' | Female parent '14.0109' | Male parent '06.0057' |
|---|---|---|---|
| Flower color | Burgundy | Purple | Pink-purple with a tiny white eye |

'KLEVP20037' is most similar to the commercial *Verbena* POPS 'Salmon+Red Eye' (also known as 'KLEVP15616', U.S. Plant Pat. No. 28,320). Differences between the varieties are described in Table 2.

TABLE 2

Comparison with Similar Variety

| Characteristic | 'KLEVP20037' | 'Salmon + Red Eye' |
|---|---|---|
| Growth habit | Upright, compact, and rounded | Upright |
| Flower color | Burgundy | Pink with colored eye |
| Branching ability | Better than 'Salmon + Red Eye' | Less than 'KLEVP20037' |

I claim:

1. A new and distinct variety of *Verbena* plant designated 'KLEVP20037' as illustrated and described herein.

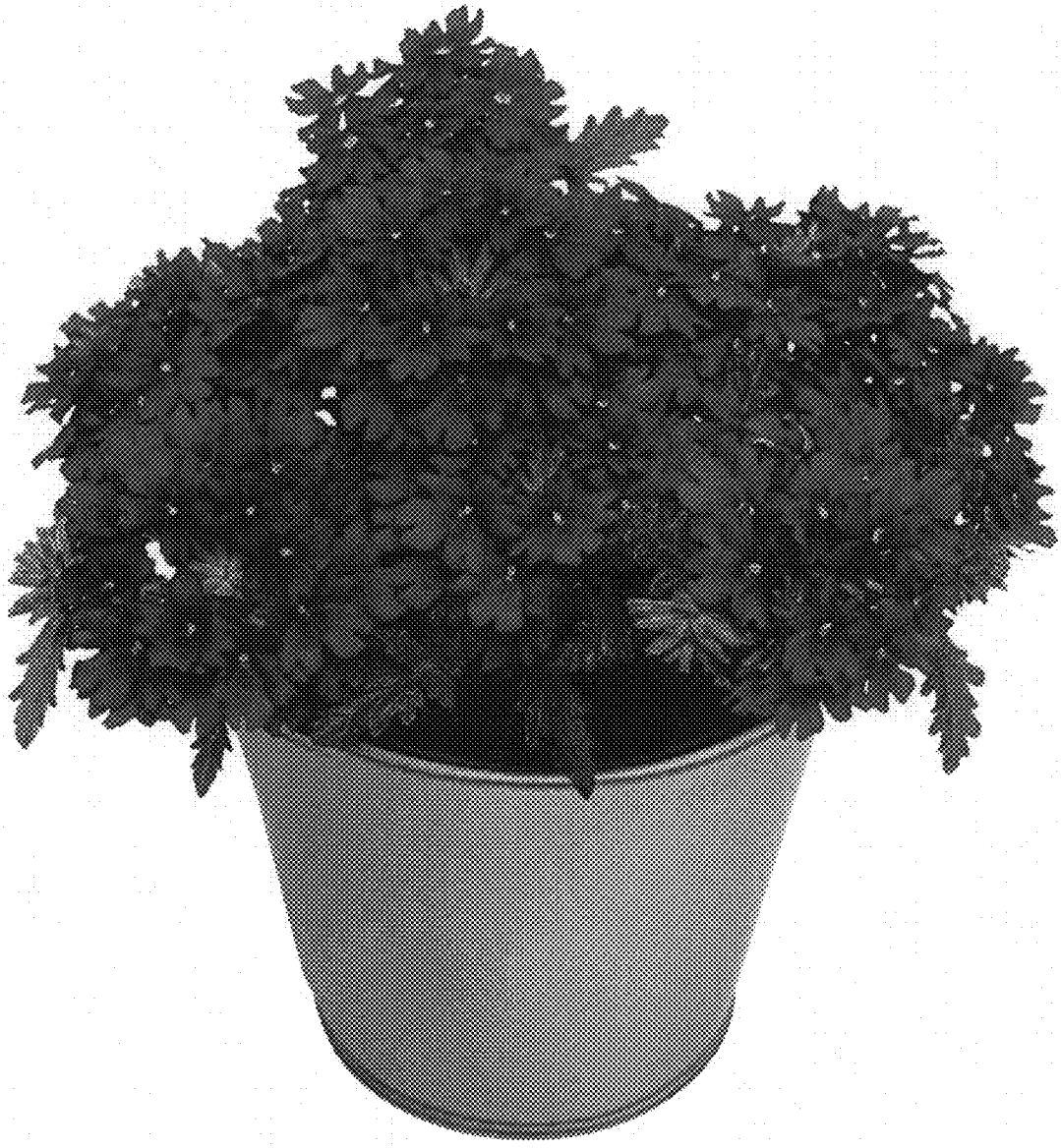

* * * * *